United States Patent [19]
Fox et al.

[11] Patent Number: 5,668,846
[45] Date of Patent: Sep. 16, 1997

[54] METHODS AND APPARATUS FOR SCANNING AN OBJECT AND DISPLAYING AN IMAGE IN A COMPUTED TOMOGRAPHY SYSTEM

[75] Inventors: Stanley H. Fox, Brookfield; Robert Senzig, Germantown; Jiang Hsieh, Waukesha, all of Wis.

[73] Assignee: General Electric Company, Milwaukee, Wis.

[21] Appl. No.: 733,502

[22] Filed: Oct. 18, 1996

[51] Int. Cl.$^6$ ............................................. A61B 6/00
[52] U.S. Cl. .......................... 378/4; 378/62; 378/901
[58] Field of Search ............................ 378/4, 901, 41, 378/42, 62; 364/413.22, 413.13

[56] References Cited

U.S. PATENT DOCUMENTS 5,251,635  10/1993  Dumoulin et al. ................. 378/47

Primary Examiner—Don Wong
Attorney, Agent, or Firm—John S. Beulick; John H. Pilarski

[57] ABSTRACT

Methods and apparatus for scanning an object in a computed tomography system during an interventional procedure are described. The computed tomography system includes an x-ray source, a detector, and a display. The detector detects x-rays projected from the x-ray source and attenuated by an object. A processor is coupled to the detector and coupled to the display for generating images of the object on the display. A helical scan is executed to generate an image slice of the object corresponding to each gantry rotation. At least one image slice and one three-dimensional image are simultaneously displayed on the display.

20 Claims, 4 Drawing Sheets

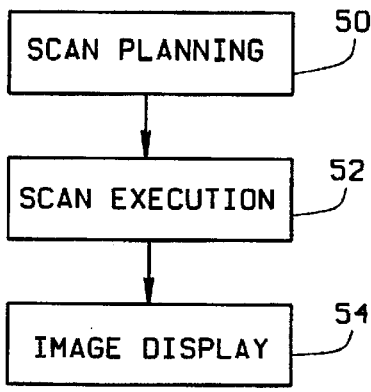

| TIME | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|------|---|---|---|---|---|---|---|---|---|----|----|----|----|----|----|----|----|----|----|----|----|----|----|----|
| SCANNING | S | S | S | A | A | S | S | S | A | A | S | S | S | A | A | S | S | S | A | A | S | S | S | |
| DISPLAY | | D1 | D2 | D3 | | | D1 | D2 | D3 | | | D1 | D2 | D3 | | | D1 | D2 | D3 | | | D1 | D2 | D3 |
100
FIG. 6
DISTANCE FROM CENTER LOCATION IN cm.
| -12 | -11 | -10 | -9 | -8 | -7 | -6 | -5 | -4 | -3 | -2 | -1 | 0 | 1 | 2 | 3 | 4 | 5 | 6 | 7 | 8 | 9 | 10 | 11 | 12 |
|-----|-----|-----|----|----|----|----|----|----|----|----|----|---|---|---|---|---|---|---|---|---|---|----|----|----|
102
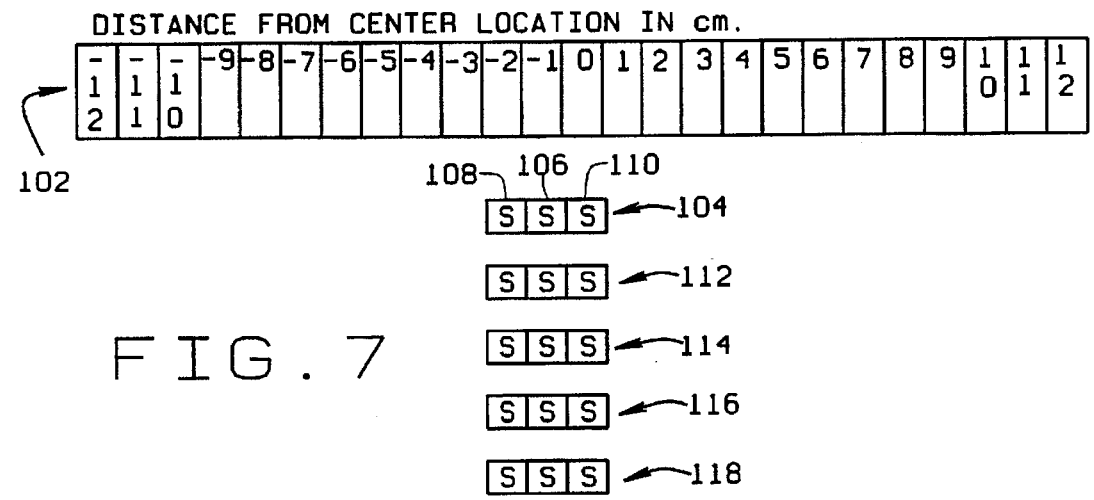
FIG. 7
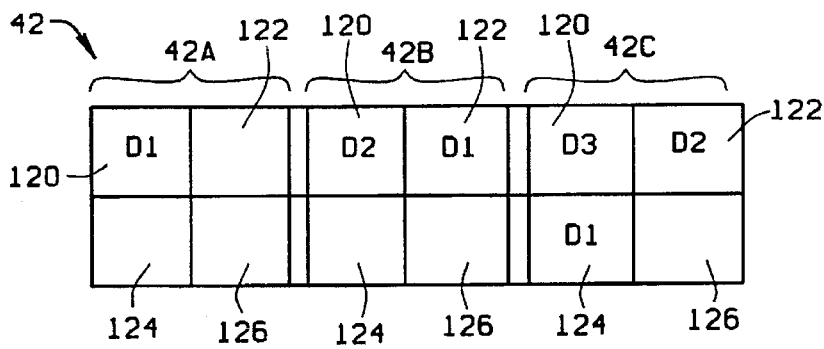
FIG. 8
| TIME | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
|------|---|---|---|---|---|---|---|---|---|----|----|----|----|----|----|----|----|----|----|----|----|----|----|----|----|----|----|
| SCANNING | S | S | S | S | S | A | A | S | S | S | S | S | A | A | S | S | S | S | S | A | A | S | S | S | S | S | |
| DISPLAY | | D1 | D2 | D3 | D4 | D5 | | | D1 | D2 | D3 | D4 | D5 | | | D1 | D2 | D3 | D4 | D5 | | | D1 | D2 | D3 | D4 | D5 |
128
FIG. 9

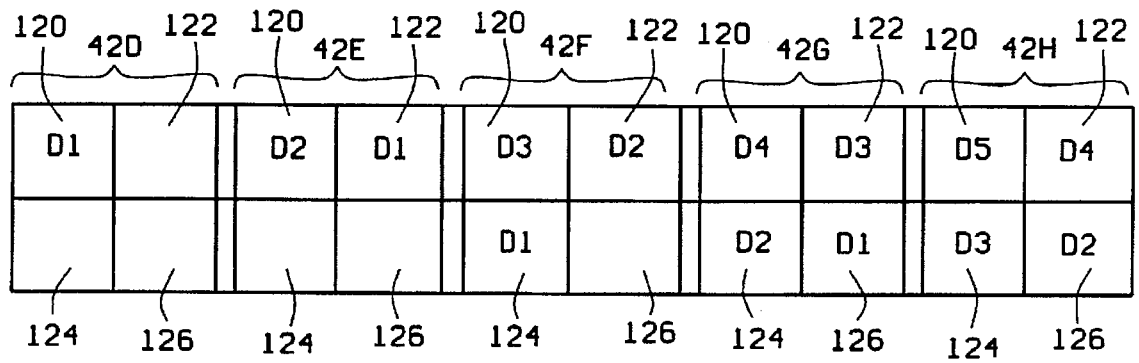
FIG. 10
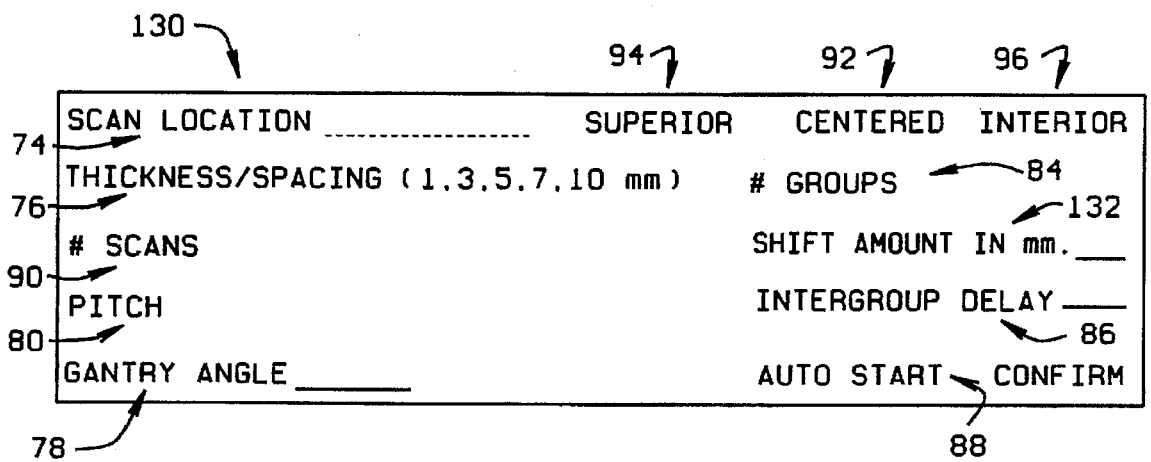
FIG. 11
FIG. 12

METHODS AND APPARATUS FOR SCANNING AN OBJECT AND DISPLAYING AN IMAGE IN A COMPUTED TOMOGRAPHY SYSTEM

FIELD OF THE INVENTION

This invention relates generally to computed tomography (CT) imaging and more particularly, to improving the quality of object scanning and image displays during interventional procedures using CT imaging.

BACKGROUND OF THE INVENTION

In at least one known CT system configuration, an x-ray source projects a fan-shaped beam which is collimated to lie within an X-Y plane of a Cartesian coordinate system, generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object.

One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed. In addition to reduced scanning time, helical scanning provides other advantages such as better control of contrast, improved image reconstruction at arbitrary locations, and better three-dimensional images.

Efforts have been undertaken to enhance the quality of CT system support for interventional procedures, such as biopsies. Significant support issues include the amount of time necessary to scan and display an image, and the quality of the displayed image. Particularly, and with respect to interventional procedures, images are not displayed in "real time," i.e., a lag exists between data acquisition, or scanning, and image display. Furthermore, known CT fluoroscopy systems typically are configured to scan at a fixed location, and display only one image slice at a time. Since the interventional procedure only proceeds as fast as the CT system acquires and displays data, such interventional procedures are done on a step-by-step, or display-by-display basis, rather than a continuing basis.

To reduce lag time, helical scans can be used for imaging during interventional procedures. However, up to 10 seconds can be required to download each helical scan. Therefore, while scan time is reduced by using a helical scan, significant down time occurs between helical scans. Moreover, and because several helical scans are needed throughout an interventional procedure, the procedure is interrupted while each helical scan is downloaded.

It would be desirable to improve CT support for interventional procedures. Particularly, it would be desirable to acquire data, reconstruct such data and display an image for such data quickly enough to guide an interventional procedure. It also would be desirable to reduce any down time during an interventional procedure, and improve the image display for interventional procedures.

SUMMARY OF THE INVENTION

These and other objects may be attained in a CT system which, in one embodiment, simultaneously and substantially in real time, displays several images to guide an interventional procedure. Particularly, and in accordance with one embodiment of the present invention, at least one image slice and one three-dimensional image are simultaneously displayed on a CT system display. To generate such images, the CT system performs multiple groups of pre-programmed helical scans. Each helical scan within a group is executed to generate multiple image slices of the object. A three dimensional image also is generated by combining image slices. At least one image slice and the three dimensional image are then simultaneously displayed so that a substantially real time three dimensional image and chronological two dimensional images are concurrently observable.

Using the above described image display method, the time lag between data acquisition and data display is reduced. Such simultaneous image display also is believed to improve CT support for interventional procedures. Furthermore, such images are believed to be generated without sacrificing overall image quality.

BRIEF DESCRIPTION OF THE DRAWINGS

FIG. 3 illustrates a sequence of steps executed during an interventional procedure.

FIG. 4 illustrates a known menu display for a CT system providing support for an interventional procedure.

FIG. 5 illustrates a menu display for a CT system providing support for an interventional procedure in accordance with one embodiment of the present invention.

FIG. 6 is a table illustrating the interaction between time, scanning and data display in accordance with one embodiment of the present invention.

FIG. 7 illustrates the scan locations for helical scans performed in accordance with one embodiment of the present invention.

FIG. 8 illustrates three successive displays of image data in accordance with one embodiment of the present invention.

FIG. 9 is a table illustrating the interaction between time, scanning and data display in accordance with one embodiment of the present invention.

FIG. 10 illustrates five successive displays of image data in accordance with one embodiment of the present invention.

FIG. 11 illustrates a menu display for a CT system providing support for an interventional procedure in accordance with one embodiment of the present invention.

FIG. 12 illustrates the scan locations for helical scans performed in accordance with one embodiment of the present invention.

DETAILED DESCRIPTION OF THE DRAWINGS

Figure 1:
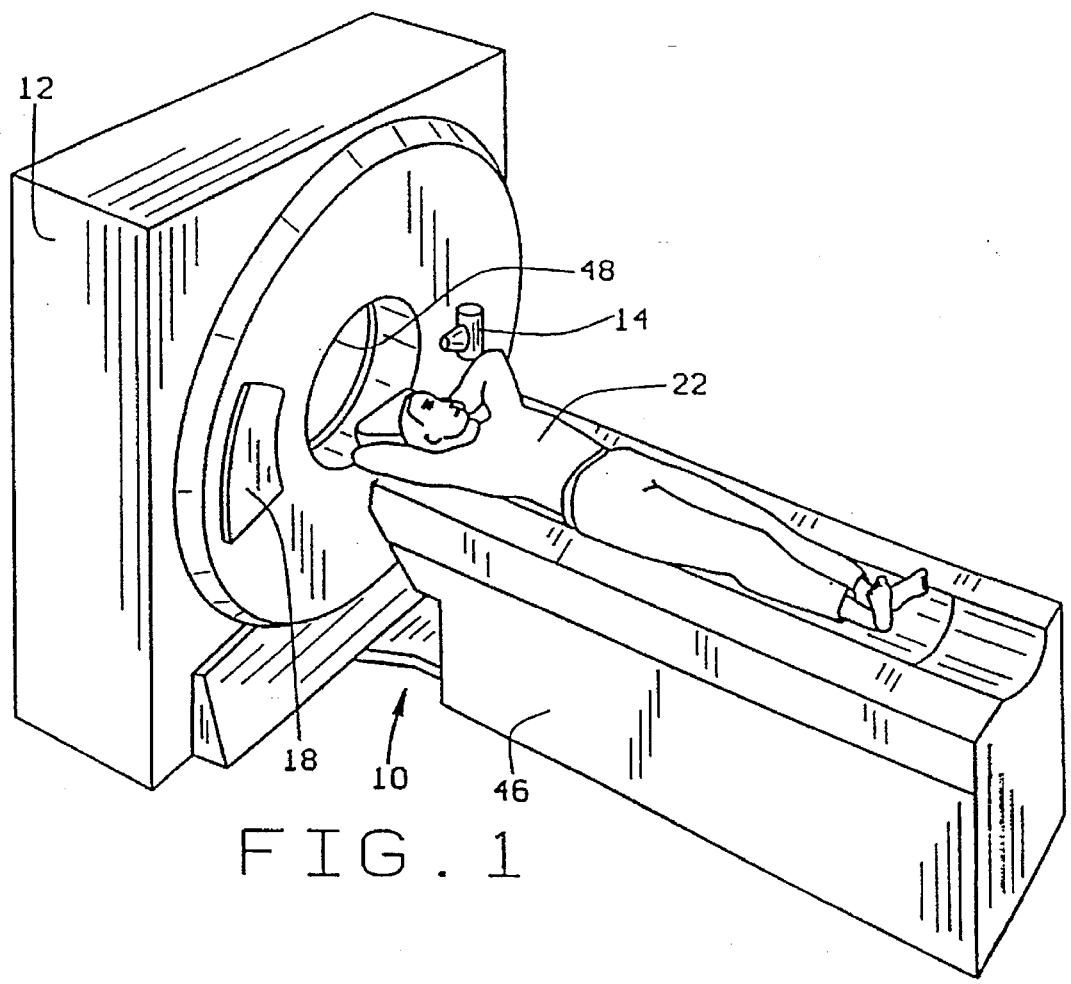
FIG. 1 is a pictorial view of a CT imaging system.
Figure 2:
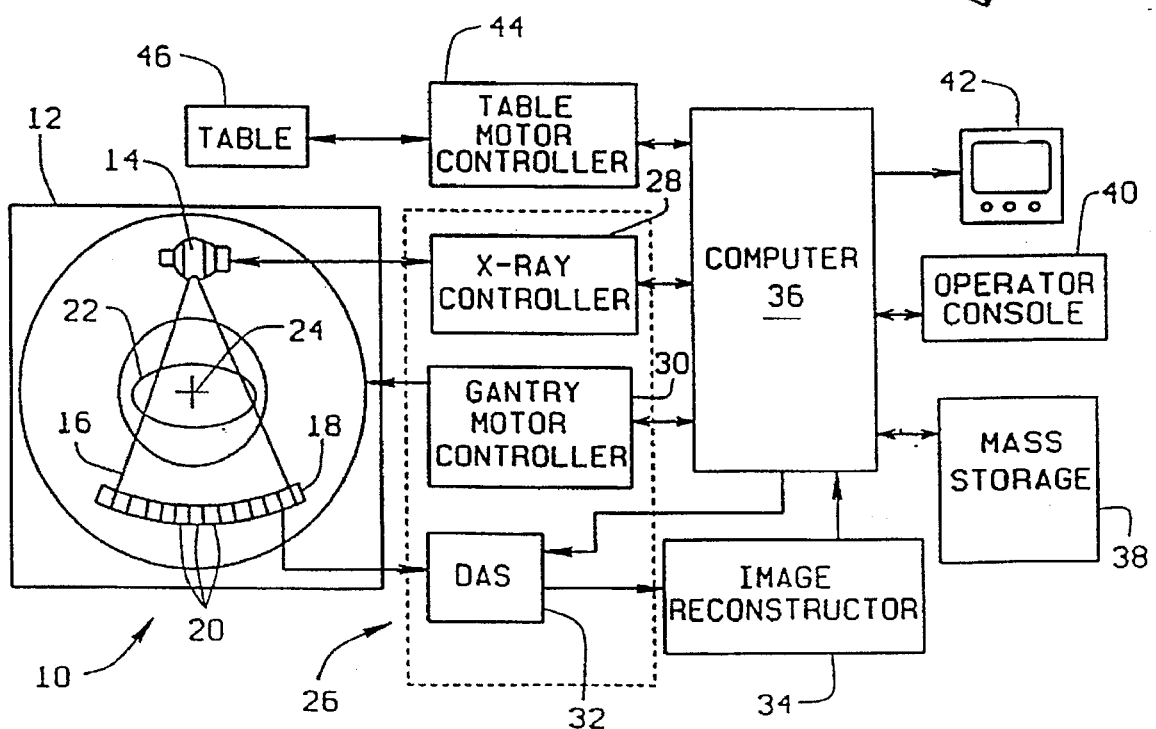
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. The present invention is not limited to practice in connection with third generation scanners and can be used, for example, in fourth generation scanners and in CT electron beam type scanners. Therefore, although the present invention is sometimes described herein in connection with third generation scanners, it should be understood that such description is by way of example only, and not by way of limitation.

With respect to system 10, gantry 12 has an x-ray source 14 that projects a beam of x-rays 16 through a source collimator (not shown) and at a gantry angle (not shown) toward a detector array 18 on the opposite side of gantry 12. Detector array 18 is formed by detector elements 10 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38. Preferably, the reconstructed image is stored as a data array.

Computer 36 also receives commands and scanning parameters from an operator via console 40 that has a keyboard. An associated display 42, such as a flat panel or a cathode ray tube display, allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. As used herein, an X mm by X mm scan refers to scanning an object of interest using an X mm collimator aperture at a 1:1 helical pitch, wherein helical pitch is the ratio of table 46 movement in one rotation of the x-ray source 14 to the slice width defined by the source collimator.

Referring to FIG. 3, and as is known, performing an interventional procedure, such as a biopsy, with CT system support typically includes a scan planning step 50, a scan execution step 52 and an image display step 54. During scan planning step 50, a patient target region (not shown) is identified. Patient 22 is positioned in gantry 12, and patient 22 is scanned to generate anatomy images of patient's anatomy surrounding the target region. A patient entry point and a path between the entry point and the target region are determined utilizing the patient's anatomy images. Patient 22 is then positioned in gantry 12 so that gantry 12 is aligned with the patient's entry point.

During scan execution step 52, an interventional tool such as a needle is inserted into the patient entry point, and advanced along the path to the target region. While advancing the needle, patient 22 is scanned to generate images identifying the location of the needle within the patient anatomy. For example, after the needle is inserted into patient 22, patient 22 is scanned to determine the location of the needle. After the scan, the needle is advanced to a new location within the patient anatomy. Patient 22 is again scanned to identify this new location of the needle. The needle is again advanced, and patient 22 again scanned, until the needle is within the target region.

During image display step 54, and using projection data collected in scan execution step 52, images are generated and displayed on display 42 so that the operator may view the location of the needle within the patient anatomy, and determine whether the needle is within the path. More particularly, sequential images are displayed on display 42 so that the operator may view, on an image-by-image basis, the advancement of the needle within the path.

During both scan execution step 52 and image display step 54, and referring to FIG. 4, a menu 56 is also displayed on display 42 so that the operator may view various commands and parameters being used during the procedure. Particularly, prior to the interventional procedure, the operator selects a scan location 58, and a scan thickness/spacing 60 for each scan to be performed. With respect to scan location 58, the operator selects whether a scan will be centered 62 with respect to patient 22, or whether a scan will be superior 64 or inferior 66 with respect to patient 22. Scan thickness 60 refers to the slice width defined by the source collimator.

Menu 56 also identifies a number of scans 68 and a gantry angle 70. For each scan, number of scans 60 increases incrementally to display the number of scans performed during a procedure. Gantry angle 70 refers to the angle between x-ray source 14 and patient 22. As shown, each parameter is displayed to the operator so that, if desired, the operator may change any parameter.

With the above-described system, one image slice typically is displayed subsequent to each scan. Although such a display is helpful in performing an interventional procedure, it would be desirable to provide improved CT support to better guide the interventional procedure. Of course, the cost associated with providing such improved support should not be excessive.

In accordance with one embodiment of the present invention, and to provide improved CT support, images are displayed in substantially "real time", and at least two images are displayed simultaneously on display 42, thus permitting simultaneous viewing of several chronological and sequential images. More specifically, and referring to FIG. 5, which illustrates a menu 72 of a system in accordance with one embodiment of the present invention, the operator may select parameters including scan location 74, scan thickness/spacing 76, gantry angle 78, Pitch 80, Fast Biopsy I/Q 82, # Groups 84, Intergroup Delay 86, Auto Start 88, and # Scans 90. Each parameter is displayed to the operator so that, if desired, the operator may change any parameter.

With respect to scan location 74, the operator selects whether a scan will be centered 92 with respect to patient 22, or whether a scan will be superior 94 or inferior 96 with respect to patient 22. Scan thickness 76 refers to the slice width defined by the source collimator, and # Scans 90 displays the number of scans performed during the procedure. Gantry angle 78 refers to the angle between x-ray source 14 and patient 22. Pitch 80 refers to helical pitch, which is the ratio of table 46 movement in one rotation of the x-ray source 14 to the slice width defined by the source collimator. Fast biopsy I/Q 82 enables an operator to select between scanning modes. One mode is described below in connection with FIGS. 6–10, and another mode is described below in connection with FIGS. 11–12.

As shown in FIG. 5 and using #Groups 84, the operator also selects a maximum number of scans to be performed as a group, i.e., a scan group. Specifically, and for example only, if the operator selects three for # Groups 84, then CT system 10 performs three continuous and successive scans without interruption, i.e., gantry 12 rotates three times. Generally, the scan trajectory is contained in a volume coverable by three to five 3–10 mm scans, i.e., a 3 to 5 cm volume. Therefore, for example, three rotations with a 2:1 pitch allow the scanned volume to be 6 cm long, thus enabling the trajectory to be scanned. In accordance with one embodiment of the present invention, a three rotation scan group is used. However, other # Groups 84 may be used, such as four or five. Similarly, both pitch 80 and gantry tilt, or gantry angle 78 can be modified, for example, to make up for any limitations of a fixed table reference.

Referring still to FIG. 5, the operator may select an Intergroup Delay 86 and an Auto Start 88. Auto Start 88, in one embodiment, is an on/off toggle which permits scanning to be done either automatically or manually, i.e., in an autostart mode or in a manual mode. Intergroup Delay 86 is a fixed delay time, or a time period in which x-ray source 14 does not project x-rays 16, i.e., x-ray source is turned off, between scanning groups when CT system 10 is in autostart mode, i.e., when the operator selects Auto Start 88. If Auto Start 88 selected, then system 10 performs the number of scans selected as # Groups 84, and performs no scanning for the delay time selected as Intergroup Delay 86. For example only, if Auto Start 88 is selected, if # Groups 84 is three, and if Intergroup Delay 86 is two seconds, then system 10 performs three scans, waits two seconds, performs three more scans, waits two more seconds, and so forth.

As explained above, the operator may select the various parameters. Particularly, operator may insert the parameters via console 40 into computer 36. Computer 36, in accordance with one embodiment, includes a memory unit configured to store # Groups 84, Intergroup Delay 86, the previously identified parameters, including scan location 74, scan thickness/spacing 76, gantry angle 78, and Pitch 80.

If the operator does not select Auto Start 88, then the delay time between groups is variable. Particularly, the operator specifically starts each group scan. For example, system 10 may further include a Start Scan switch (not shown) permitting the operator to manually start a group scan. The Start Scan switch is then activated for a selected # Groups 84. After each group scan, the operator must reactivate the switch for a subsequent group scan. Therefore, the operator may vary the delay time between group scans by merely waiting longer or shorter to begin a subsequent group scan.

Referring now to FIG. 6, a table 100 is shown illustrating the interaction between time, scanning and image display in accordance with one embodiment of the present invention. Particularly, and for example only, FIG. 6 represents a system 10 in which each gantry rotation takes approximately one second, image data acquired during each gantry rotation may be displayed as an image within one second of acquisition, # Groups 84 is three, Auto Start 88 is selected, and Intergroup Delay 86 is two seconds. As shown, system 10 first performs three scans (S), or a group scan, in accordance with the selected # Groups 84. After the first group scan, system 10 performs no scans, i.e., x-ray source 14 is turned off, for two seconds, in accordance with the selected Intergroup Delay 86. Moreover, as shown and in accordance with image display step 54, an image corresponding to each individual scan is displayed (D1, D2, or D3) within one second after the scan, i.e., in substantial "real time."

As shown in FIG. 6, the needle may be adjusted (A) within patient 22 during Intergroup Delay 86. Particularly, and as shown, a three rotation scan group, i.e., where # Groups 84 is three, permits four needle adjustments in a twenty second period, or in one breath hold. It also allows four tries when breath hold adjustments are used to move the target lesion into view. The whole series could be repeated in another twenty seconds.

Referring now to FIG. 7, a table 102 illustrates exemplary scan locations for helical scans. For example, and as shown, a first group scan 104 is centered. Here, # Groups 84 is three and, as shown, one scan 106 of first group scan 104 is centered at 0 cm, while the other two scans 108 and 110 of first group scan 104 are immediately adjacent one scan 106, and on opposite sides of one scan 106, at −1 cm and 1 cm, respectively. Each subsequent group scan 112, 114, 116, and 118, as shown, is similarly centered.

Referring to FIG. 8, display 42 is configured to be a 1024×1024 pixel, 4 on 1, first-in first-out display. Particularly, display 42 is configured to have a first portion 120, a second portion 122, a third portion 124 and a fourth portion 126. As shown in FIG. 8, display 42 has three successive and chronological displays of image data 42A, 42B, and 42C. A first image (D1) generated from a first scan is displayed on first portion 120. Subsequently, and after a second scan, a second image (D2) generated from the second scan is displayed on first portion 120 while first image (D1) is simultaneously displayed on second portion 122. Similarly, after a third scan generates a third image (D3), third image (D3) is displayed on first portion 120 while second image (D2) is simultaneously displayed on second portion 122 and first image (D1) is simultaneously displayed on third portion 124. In accordance with one embodiment, second image (D2) is color coded or grey scale shifted to indicate temporal differences between second image (D2) and first image (D1). Similarly, third image (D3) may be color coded or grey scale shifted to indicate temporal differences between third image (D3) and second image (D2).

Fourth portion 126 is configured to display a three dimensional image corresponding to each scanned image, or a combination of some of the scanned images. For example, a three dimensional image may be created from first image (D1) and displayed in fourth portion 126. Subsequently, after generation of second image (D2), an updated three dimensional image may be created from first image (D1) and second image (D2) and displayed in fourth portion 126. Similarly, after generation of third image (D3), a further updated three dimensional image may be created from first image (D1), second image (D2), and third image (D3), and displayed in fourth portion 126. Alternatively, and for example, a further updated three dimensional image may be created from only first image (D1) and third image (D3). In accordance with one embodiment, the color coding in second image (D2) and third image (D3) is blended so that the three dimensional image identifies the temporal differences between third image (D3) and second image (D2).

The three dimensional image, in one embodiment, may be nutated with a nutation angle to display the three dimensional image from varying points of view. Three dimensional rendering techniques that could be used include MPVR, a shaded surface display, or other known volume rendering techniques, such as techniques employing selective opacity, perspective, variable point of view, and planar windows.

Referring now to FIG. 9, a table 128 illustrates the interaction between an exemplary time, scanning and image display. Specifically, FIG. 9 illustrates system 10 in which a five scan group, i.e., # Groups 84 is 5, is selected and an Intergroup Delay 86 of two seconds is selected. As shown, system 10 first performs five scans, or a group scan, in accordance with the selected # Groups 84. After the first group scan, system 10 performs no scans for two seconds, in accordance with the selected Intergroup Delay 86. Moreover, as shown and in accordance with image display step 54, an image corresponding to each individual scan is displayed within one second after the scan, i.e., in substantial "real time."

As shown in FIG. 9, the needle may be adjusted (A) within patient 22 during Intergroup Delay 86. Particularly, a five rotation scan group, i.e., where # Groups 84 is five, permits three needle adjustments in a twenty second period, or in one breath hold. It also allows three tries when breath hold adjustments are used to move the target lesion into view. The whole series could be repeated in another twenty seconds.

FIG. 10 illustrates five successive and chronological displays of image data 42D, 42E, 42F, 42G, and 42H, in accordance with one embodiment of the present invention. As shown, a first image (D1) is generated from a first scan is displayed on first portion 120. Subsequently, and after a second scan, a second image (D2) generated from the second scan is displayed on first portion 120 while first image (D1) is simultaneously displayed on second portion 122. Similarly, after a third scan generates a third image (D3), third image (D3) is displayed on first portion 120 while second image (D2) is simultaneously displayed on second portion 122 and first image (D1) is simultaneously displayed on third portion 124. Similarly, after a fourth scan generates a fourth image (D4), fourth image (D4) is displayed on first portion 120 while third image (D3) is simultaneously displayed on second portion 122 and second image (D2) is simultaneously displayed on third portion 124 and first image (D1) is simultaneously displayed on fourth portion 126. Further, after a fifth scan generates a fifth image (D5), first image D1 is removed from display 42, while images D5, D4, D3, D2 are displayed as shown. In one embodiment, all displayed images are removed from display 42 when displaying a first image from a subsequent group.

In yet another embodiment, and as described above, fourth portion 126 may be configured to display a three dimensional image corresponding to each scanned image. In this embodiment, three other images are displayed on display 42. Alternatively, display 42 may be configured to have more than four portions, to permit simultaneous display of more than four images. Similarly, display 42 may be configured to have fewer than four portions, to permit simultaneous display of fewer than four images. For example, display 42 may be configured to have three portions, wherein a first and a second portion are configured to display a first and a second image slice, respectively, and a third portion is configured to display a three dimensional image.

Referring to FIG. 11, which illustrates a menu 130 of a system in accordance with yet another embodiment of the present invention, the operator may select additional parameters including Shift Amount in mm 132, which permits the operator to "bump" selected scan location 58 a fixed distance in either the inferior or superior direction between group scans. Particular, the operator may select a shift amount in mm, and a shift direction, i.e., superior or inferior and thus adjust the location of subsequent group scans.

For example, and referring to FIG. 12, a first group scan 134, with no shift in location, is centered at 0 mm. As shown, FIG. 12 illustrates scanning where # Groups 84 is five. If the operator selects a 50 mm shift in the inferior direction, i.e., Shift Amount in mm 132 is fifty mm inferior, a second group scan 136 will shift so that it is centered 50 mm inferior of the first group scan 134, i.e., at −5 cm. Subsequently, if the operator selects a 50 mm shift in the superior direction, i.e., Shift Amount in mm 132 is fifty mm superior, a third group scan 138A will again be centered at 0 mm. Alternatively, if the operator selects a 50 mm shift farther in the inferior direction, i.e., Shift Amount in mm 132 is fifty mm inferior, a third group scan 138B would be centered at −10 cm. While 50 mm increments are used in this example, any size increment could be used. Each adjustment is believed to take no more than one second to load. Therefore, the time line would be the same as described above in reference to FIG. 9.

Shift Amount in mm 132 is believed to allow for tracking of the needle to the target if the path is too oblique, if patient 22 breathes differently than in scan planning step 50, or if patient 22 does not completely suspend respiration.

The above-described embodiments may also be used in connection with a multislice CT system. Known multislice scanners typically have multiple rows of detectors per slice. For example, a two slice detector has two rows of detectors, and a four slice detector has four rows of detectors. Accordingly, an axial scan with a multislice CT system generates multiple image slices. In accordance with one embodiment of the present invention, the # Groups 84 refers to a maximum number of detector rows selected to contribute to image display. Specifically, and for example only, if the operator selects a scan group of three for # Groups 84, then the multislice CT system performs a scan and displays image slices corresponding to three rows of detectors.

It is contemplated that to improve image quality, the portion of the image displaying the needle can be removed, e.g., filtered out, and replaced by a model needle image prior to display. Using such model also may enable better planning the needle trajectory since the location of the needle relative to the target may be more precisely observed using such a model. In addition, a scan may be performed while the needle is placed at the patient entry point, and a model needle image may be generated. Based on the needle location and orientation, the desired needle placement, i.e., patient entry point, and needle orientation can be determined before inserting the needle into patient 22. A model also can be generated once an entry point and needle orientation are selected to show the needle trajectory resulting from such entry point and orientation. It also is contemplated that an external sensory device can be used to provide guidance to the needle or interventional instrument placement.

The above-described embodiments minimize time lag between data acquisition and data display. Further, the embodiments permit simultaneous display of several images. Simultaneous image display is believed to improve CT support for interventional procedures by permitting simultaneous and nearly instantaneous displays of two dimensional slices and three dimensional images. Furthermore, the overall image quality is not reduced.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Similarly, the present invention may be used in connection with electron beam systems, which are well known in the art and are sometimes referred to as CT electron beam systems. Furthermore, while the CT system described herein acquires single slices, other systems could be used which acquire 2, 4, or more slices simultaneously. Accordingly, the spirit and scope of the invention are to be limited only by the terms of the appended claims.

What is claimed is:

1. A method for scanning an object in a computed tomography system, the computed tomography system including an x-ray source for projecting x-rays, a detector for detecting x-rays from the x-ray source and attenuated by the object, a display, and a processor coupled to the detector and coupled to the display for generating images on the display, said method comprising the steps of:

obtaining scan projection data;

processing the projection data to generate image data; and displaying at least one image slice and one three-dimensional image simultaneously on the display.

2. A method in accordance with claim 1 wherein the display has at least three portions, and said method comprises simultaneously displaying a first image slice on a first display portion, a second image slice on a second display portion, and a three-dimensional image on a third display portion.

3. A method in accordance with claim 1 wherein the x-ray source and detector are mounted on a gantry which rotates around the object, and obtaining scan projection data comprises the steps of:

selecting a scan group to determine a maximum number of gantry rotations;

selecting an intergroup delay to determine a period of time in which the x-ray source does not project x-rays; and using said selected scan group and said selected intergroup delay to execute the scan.

4. A method in accordance with claim 3 wherein said selected scan group comprises at least two gantry rotations.

5. A method in accordance with claim 3 wherein the computed tomography system further includes a memory unit coupled to said processor, and wherein said method further comprises the step of storing the selected scan group in the memory unit.

6. A method in accordance with claim 5 wherein said method further comprises the step of storing the selected intergroup delay in the memory unit.

7. A method in accordance with claim 4 wherein the display has four portions, and said method comprises simultaneously displaying a first image slice on a first display portion, a second image slice on a second display portion, a third image slice on a third display portion, and a three-dimensional image on a fourth display portion.

8. A method in accordance with claim 7 wherein simultaneously displaying the first image slice, the second image slice, the third image slice, and the three-dimensional image comprises the steps of color coding the second image slice to indicate temporal differences between the second image slice and the first image slice, and color coding the third image slice to indicate temporal differences between the third image slice and the second image slice.

9. A method in accordance with claim 3 wherein obtaining scan projection data further comprises the step of selecting a scan location.

10. A method in accordance with claim 3 wherein obtaining scan projection data further comprises the steps of:

determining a patient entry point;

placing an interventional instrument at said determined patient entry point;

determining an interventional instrument orientation at said determined patient entry point; and identifying an interventional instrument trajectory.

11. A method in accordance with claim 3 wherein the computed tomography system further includes an external sensory device, and wherein obtaining scan projection data further comprises the steps of:

determining a patient entry point;

placing an interventional instrument at said determined patient entry point; and providing guidance to the interventional instrument using the external sensory device.

12. A processor for a computed tomography system including an x-ray source for projecting x-rays, a detector for detecting x-rays from the x-ray source and attenuated by an object, and a display, said processor coupled to the detector and coupled to the display for generating images on the display, said processor programmed to:

obtain scan projection data;

process the projection data to generate image data; and display at least one image slice and one three-dimensional image simultaneously on the display.

13. A processor in accordance with claim 12 wherein the display has at least three portions, and said processor is programmed to simultaneously display a first image slice on a first display portion, a second image slice on a second display portion, and a three-dimensional image on a third display portion.

14. A processor in accordance with claim 12 wherein the x-ray source and the detector are mounted on a gantry which rotates around the object, and to obtain the scan projection data, said processor is further programmed to:

select a scan group to determine a maximum number of gantry rotations;

select an intergroup delay to determine a period of time in which the x-ray source does not project x-rays; and use said selected scan group and said selected intergroup delay to execute the scan.

15. A processor in accordance with claim 14 wherein said selected scan group comprises at least two gantry rotations.

16. A processor in accordance with claim 14 wherein the computed tomography system further includes a memory unit configured to store the selected scan group, and said processor is coupled to the memory unit.

17. A processor in accordance with claim 15 wherein the display has four portions, and said processor is programmed to simultaneously display a first image slice on a first display portion, a second image slice on a second display portion, a third image slice on a third display portion, and a three-dimensional image on a fourth display portion.

18. A processor in accordance with claim 17 wherein to simultaneously display the first image slice, the second image slice, the third image slice, and the three-dimensional image, said processor is programmed to color code the second image slice to indicate temporal differences between the second image slice and the first image slice, and to color code the third image slice to indicate temporal differences between the third image slice and the second image slice.

19. A processor in accordance with claim 18 wherein to display the three-dimensional image, said processor is programmed to blend the color code of the second image slice and color code of the third image slice so that the three-dimensional image indicates the temporal differences between the second image slice and the third image slice.

20. A processor in accordance with claim 12 wherein to display the three-dimensional image, said processor is programmed to nutate the three-dimensional image with a nutation angle to display the three-dimensional image from varying points of view.

* * * * *